United States Patent [19]

Fieldsteel et al.

[11] Patent Number: 4,464,470

[45] Date of Patent: Aug. 7, 1984

[54] REPLICATION OF VIRULENT TREPONEMA PALLIDUM IN TISSUE CULTURE

[75] Inventors: A. Howard Fieldsteel, Cupertino; David L. Cox, East Palo Alto; Randolph A. Moeckli, Mountain View, all of Calif.

[73] Assignee: SRI International, Menlo Park, Calif.

[21] Appl. No.: 343,353

[22] Filed: Jan. 27, 1982

Related U.S. Application Data

[63] Continuation-in-part of Ser. No. 237,917, Feb. 25, 1981, abandoned.

[51] Int. Cl.$^3$ .......................... C12N 1/20; C12N 5/00; C12N 1/00; C12N 1/36; C12N 1/04
[52] U.S. Cl. ..................................... 435/253; 435/240; 435/243; 435/245; 435/260
[58] Field of Search ............... 435/240, 243, 253, 260, 435/245; 424/92, 93, 88

[56] References Cited

U.S. PATENT DOCUMENTS

| | | | |
|---|---|---|---|
| 2,255,079 | 9/1941 | Morrison et al. | 435/253 |
| 2,513,327 | 7/1950 | Ichelson | 435/258 |
| 2,709,670 | 5/1955 | Ichelson | 435/7 |
| 3,502,546 | 3/1970 | Thompson et al. | 435/42 |
| 4,098,646 | 7/1978 | Jones et al. | 435/240 |

OTHER PUBLICATIONS

Netzer: Genetic Engineering News 2(6), Nov.-Dec. 1982.
Norris et al.; Infect. Imm. 22, 689, (1978).
Alderete et al.; Infect. Imm. 26, 1048, (1979).
Norris: Infect. Imm. 36, 437, (1982).
Graves et al., Retention of Motility and Virulence of *T. pallidum* in vitro: Infection and Immunity, 1975, 12(5), 1116–1120, (USA).
Boak et al., Studies on the Cultivation of *T. pallidum*, American Journal of Syphilis, Gonorrhea, Veneral Diseases 33, 409–415, (1942).
Fitzgerald, The Future of Tissue Culture Methods for Growth of *Treponema pallidum* in vitro, Sexually Transmitted Diseases, Apr.-Jun., 1980, pp. 97–99.
Musher et al.—The Role of a Vaccine for Syphilis—ibid Oct.-Dec. 1977, pp. 163–166.
Cox, C. D. and M. K. Barber, 1974, Oxygen Uptake by *Treponema pallidum*, Infect. Immun. 10:123–127.
Fieldsteel, A. H., F. A. Becker, and J. G. Stout, 1977, Prolonged Survival of Virulent *Treponema pallidum*, (Nichols Strain) in Cell-Free and Tissue Culture Systems, Infect. Immun. 18:173–182.
Fieldsteel, A. H., D. L. Cox, and R. A. Moeckli, 1981, Cultivation of Virulent *Treponema pallidum* in Tissue Culture, Infect. Immun. 32:908–915.
Fieldsteel, A. H., J. G. Stout, and F. A. Becker, 1981, Role of Serum in Survival of *Treponema pallidum* in Tissue Culture, in vitro 17:28–32.
Fitzgerald, T. J., R. C. Johnson, J. A. Sykes, and J. N. Miller, 1977, Interaction of *Treponema pallidum* (Nichols Strain) with Cultured Mammalian Cells: Effects of Oxygen, Reducing Agents, Serum Supplements, and Different Cell Types, Infect. Immun. 15:444–452.
Kimm, G. E., R. H. Allen, M. J. Morton, and J. F. Morgan, 1962, Studies on the in vitro Survival of Virulent *Treponema pallidum*, Am. J. Hyg. 75:339–356.
Nelson, R. A. Jr., 1948, Factors Affecting the Survival of *Treponema pallidum* in vitro, Am. J. Hyg. 48:120–132.
Sandok, P. L., L. M. Jenkin, H. M. Matthews, and M. S. Roberts, 1978, Unsustained Multiplication of *Treponema pallidum* (Nichols Virulent Strain) in vitro in the Presence of Oxygen, Infec. Immun. 19:421–429.
Turner, T. B. and D. H. Hollander, 1957, Biology of the Treponematoses, W.H.O. Monogr. Ser. No. 35.
Weber, M. M., 1960, Factors Influencing the in vitro Survival of *Treponema pallidum*, Am. J. Hyg. 71:401–417.

*Primary Examiner*—Thomas Wiseman
*Assistant Examiner*—James Martinell
*Attorney, Agent, or Firm*—Alex Mazel

[57] ABSTRACT

A method and materials are provided for replication of virulent *Treponema pallidum* in tissue culture, employing a modified Eagle's minimum essential medium, wherein said in vitro cultivated *T. pallidum* can be utilized as a source of relatively pure organisms, free of host tissue, for the preparation of a vaccine against syphilis and as a source of organisms for use in specific immunological tests for syphilis.

15 Claims, 2 Drawing Figures

REPLICATION OF VIRULENT TREPONEMA PALLIDUM IN TISSUE CULTURE

ORIGIN OF INVENTION

The work upon which the present application is based was supported by Public Health Service Research Grant R01 A1 115 113 from the National Institue of Allergy and Infectious Diseases.

RELATED APPLICATION

This is a continuation-in-part of U.S. Ser. No. 237,917 filed Feb. 25, 1981 now abandoned.

BACKGROUND OF THE INVENTION

The development of a vaccine for syphilis has been hindered by inability to culture the causative organism *Treponema pallidum* in vitro. Reports of successes have been published, but when identical procedures were attempted by different investigators, multiplication was not detected. In order to achieve the necessary cultivation, it is essential that a method be reproducible in other laboratories before it can be called successful. Thus, see the following U.S. Pat. Nos. 2,255,079, 2,513,327, 2,709,670, 3,502,546 and 4,098,646. Additionally, see Graves et al, Retention of Motility and Virulence of *T. pallidum* in vitro; Infection and Immunity. 1975, 12(5) 1116–20 (U.S.A.),—Serzhantova, Growth of *T. pallidum*, in a Thioglycollate Medium Vestn. Dermatol. 1969, 43(8) 48–51 (Russian),—Boak et al, Studies on the Cultivation of *T. pallidum*, American Journal of Syphillis, Gonorrhea, Venereal Diseases 33, 409–15 (1942). See also Fitzgerald, The Future of Tissue Culture Methods for Growth of *Treponema pallidum* in vitro, Sexually Transmitted Diseases April–June, 1980, pp 97–99,—and Musher et al.—The Role of A Vaccine for Syphilis—ibid October–December 1977, pp 163–166, Cox, C. D. and M. K. Barber. 1974. Oxygen uptake by *Treponema pallidum*. Infect. Immun. 10:123–127.

Fieldsteel, A. H., F. A. Becker, and J. G. Stout. 1977. Prolonged survival of virulent *Treponema pallidum* (Nichols strain) in cell-free and tissue culture systems. Infect. Immun. 18:173–182.

Fieldsteel, A. H., D. L. Cox, and R. A. Moeckli. 1981. Cultivation of virulent *Treponema pallidum* in tissue culture. Infect. Immun. 32:905–915.

Fieldsteel, A. H., J. G. Stout, and F. A. Becker. 1981. Role of serum in survival of *Treponema pallidum* in tissue culture. In Vitro 17:28–32.

Fitzgerald, T. J., R. C. Johnson, J. A. Sykes, and J. N. Miller. 1977. Interaction of *Treponema pallidum* (Nichols strain) with cultured mammalian cells: Effects of oxygen, reducing agents, serum supplements, and different cell types. Infect. Immun. 15:444–452.

Kimm, G. E., R. H. Allen, M. J. Morton, and J. F. Morgan. 1962. Studies on the in vitro survival of virulent *Treponema pallidum*. Am. J. Hyg. 75:339–356.

Nelson, R. A., Jr. 1948. Factors affecting the survival of *Treponema pallidum* in vitro. Am. J. Hyg. 48:120–132.

Sandok, P. L., H. M. Jenkin, H. M. Mattews, and M. S. Roberts. 1978. Unsustained multiplication of *Treponema pallidum* (Nichols virulent strain) in vitro in the presence of oxygen. Infect. Immun. 19:421–429.

Turner, T. B. and D. H. Hollander. 1957. Biology of the treponematoses. W.H.O. Monogr. Ser. No. 35.

Weber, M. M. 1960. Factors influencing the in vitro survival of *Treponema pallidum*. Am. J. Hyg. 71:401–417.

As an almost natural sequel to the discovery that *Treponema pallidum* is the causative agent of syphilis, attempts were made to cultivate it. Although many investigators have claimed to have cultivated it in vitro, none of the isolated strains have been pathogenic or have been shown to have a causal relationship to treponemal disease in humans. Furthermore, investigators who carried out serologic studies on the cultivable Nichols, Noguchi, Reiter, Kazan, and Kroo strains of supposed *T. pallidum* found that these strains fell into three distinct serological groups and that they were morphologically and antigenically different from *T. pallidum*. Hence they questioned the identification of these treponemes as strains of *T. pallidum*. More recently, the inventors herein utilized biochemical analysis to determine whether there are genetic relationships between virulent *T. pallidum* and five avirulent cultivable treponemes isolated from humans. Not only did the deoxyribonucleic acid (DNA) base composition (G+C content) of the cultivable treponemes differ markedly from that of *T. pallidum*, but saturation reassociation assays revealed no detectable DNA sequence homology. Consequently, the nonpathogenic cultivable treponemes studied were neither variants nor mutants of *T. pallidum* and were actually genetically distinct organisms.

Originally it had been generally assumed that *T. pallidum* was an anaerobic organism because it survived poorly under aerobic conditions. Therefore, in attempts to obtain survival and/or replication of *T. pallidum* in vitro, anaerobic conditions were maintained and reducing agents were added to media to lower the oxidation-reduction potential. Although the 50% survival time ($ST_{50}$) of *T. pallidum* under these conditions was as long as 16 days, there apparently was no correlation between the $ST_{50}$ and virulence for rabbits, which was lost after 6 days in vitro.

Despite the apparent anaerobic nature of treponemes, the presence of cytochromes has been demonstrated in the nonpathogenic cultivable Reiter treponeme (*T. phagedenis* biotype Reiter) which suggested possible utilization of molecular oxygen under certain conditions. More recently, it has been shown that *T. pallidum* consumed oxygen at the same rate as did a known aerobic spirochete, Leptospira. The oxygen uptake of the former was cyanide-sensitive, indicating that *T. pallidum* contained a functioning cytochrome oxidase system and therefore should be capable of aerobic respiration. In a study on the mechanisms involved in terminal electron transport by *T. pallidum*, these observations were confirmed, leaving little doubt as to the capabilities of virulent *T. pallidum* for aerobic respiration. Therefore, in view of the failure of all attempts to cultivate *T. pallidum* under anaerobic conditions, it appeared more than likely that oxygen is a requirement for in vitro replication.

Between 1913 and 1948, sporadic attempts were made to cultivate *T. pallidum* in tissue culture of mammalian tissues, with uniformly negative results. Recently, there has been renewed interest in the cultivation of *T. pallidum* in mammalian cell cultures. Several investigators, using both aerobic and anaerobic culture systems, have reported the attachment of *T. pallidum* to tissue culture cells, with periods of survival ranging from 24 hours to 23 days. Survival appeared to be best under conditions of low oxygen tension (3%) and when reducing agents were added to the medium. However, there was little or no evidence that the treponemes had replicated.

For example, in 1976, Jones et al. (British Journal of Venereal Diseases 52:18-23) claimed to have demonstrated replication and subculture of pathogenic *T. pallidum* in cultures of baby hamster kidney, but Foster et al. (ibid) 53:338-339 failed to corroborate these results. Others demonstrated what they called "unsustained multiplication" of *T. pallidum* in cultures under reduced oxygen tension, both in the presence and absence of mammalian cells. Virulence of the treponemes decreased as a function of time in vitro.

SUMMARY OF THE INVENTION

The original source of virulent *T. pallidum* is the testes of rabbits previously inoculated intratesticularly. The organisms are extracted from minced testes in tissue culture medium. The testis extraction medium and the tissue culture medium utilized for growing *T. pallidum* is a modified Eagle's minimum essential medium (MEM) which is made by combining the following components in distilled water to a final volume of 100 ml: 10 ml of 10× Earle's balanced salt solution without phenol red and NaHCO3, 2 ml of 50× MEM amino acids, 1 ml of 100× MEM vitamins, 1 ml of 200 mM L-glutamine, 1 ml of 100× MEM nonessential amino acids, 1 ml sodium heparin solution containing 100 U/ml, and 150 mg glucose. The solution is gassed briefly with CO2, then 3.38 ml NaHCO3 (7.5%), 3.13 ml 1M HEPES (organic buffer), 0.63 ml resazurin (20 mg%), 10 mg sodium pyruvate, and 10 mg DTT are added. The solution is filter-sterilized, and 25 ml heat-inactivated fetal bovine serum (FBS) or calf is added. This culture medium is called BRMM (Basal Reduced Medium, Modified). The flask of medium is then alternatively evacuated and gassed with 5% CO2/95% N2 mixture 3 times, and stored overnight before use.

Two to four days prior to infection with *T. pallidum*, tissue culture flasks or prescription bottles are seeded with cottontail rabbit epithelium (Sf1Ep) cells in MEM plus 10% FBS, and incubated at 33 degrees C. Prior to inoculation of the treponems the medium is removed from the flasks and replaced with 10 ml of BRMM. The cultures are gassed with 5% CO2/05% N2 for 1 minute at 3 liters/minute, and allowed to equilibrate for 4-5 hours before inoculation. The freshly harvested testis extract containing *T. pallidum* is then diluted in treponeme-free testis extract (supernate of infected extract centrifuged at 12,000× g for 10 minutes) such that 0.34 ml contains the desired number of treponemes to be inoculated into each flask. This also results in the BRMM containing a 1:30 concentration of the testis extract, which we had previously determined to be essential to the survival of *T. pallidum* in tissue culture. It is also possible to substitute testis extract from uninoculated rabbits. Further, it is possible to use the extract fresh or freeze it at −80° C. and thaw just prior to use as designated here. The cultures are then gassed for 1 minute with 1.5% O2, 5% CO2, and 93.5% N2 at 3 liters/minute, and incubation carried out at 33 degrees C. Cultures are then sacrificed at various intervals up to 12 days. When the inoculum is $1 \times 10^6$ treponemes there will be up to 100-fold increase in *T. pallidum* by the ninth day of incubation. These treponemes have been found to be virulent. After intradermal inoculation into rabbits, erythematous indurated lesions containing *T. pallidum* appear.

In a series of examples herewith, the virulent Nichols strain of *Treponema pallidum* was shown to attach and replicate on the surface of tissue culture cells of cottontail rabbit epithelium (Sf1Ep) growing in conventional monolayer cultures under a dissolved oxygen tension of 1.5%. Five days after inoculation of $10^6$ *T. pallidum*, the number of treponemes had increased to between $8 \times 10^6$ and $2.59 \times 10^7$. The viability of harvested organisms ranged from 86 to 97%. The number of *T. pallidum* continued to increase, generally reaching a plateau between the 9th and 12th day of incubation, with increases ranging up to 100-fold and averaging 49-fold. There appeared to be a ceiling of multiplication of about $2 \times 10^8$ irrespective of the inoculum, which ranged from $1 \times 10^6$ to $1 \times 10^8$ *T. pallidum*. In each experiment, organisms were harvested from the group inoculated with $1 \times 10^6$ *T. pallidum* after 7 days of incubation to test for virulence. In all instances the organisms were virulent; erythematous, indurated, treponeme-containing lesions were produced from an average of 6 to 7 organisms. Scanning electron microscopy revealed that during the course of replication many microcolonies of treponemes formed on the surface of the cells.

A number of parameters aimed at optimizing culture conditions for both Sf1Ep cells and *Treponema pallidum* have also been investigated. Optimum temperature for replication of *T. pallidum* ranged between 33° and 35° C. At 33° C., replication occurred in the presence of concentrations of atmospheric oxygen from <0.3% to 10%, with the optimum range being 1.5 to 5%. No replication occurred in the presence of 12.5% oxygen. When both temperature and oxygen concentrations were varied between 33° and 35° C. and 1.5 to 5%, respectively, little differences in replication were noted. Although variation in the oxygen concentration within each temperature group had little or no effect on replication, it did have an effect on motility, which remained greater in the 5% oxygen concentration after 9 to 12 days of cultivation. Optimum concentration of fetal bovine serum (FBS) in the culture medium was 20%, although replication occurred in concentrations ranging from 5 to 30%. If carefully screened, calf serum could be substituted for FBS. Testis extract was an essential component in the culture medium. Although that obtained from adult rabbit—either normal or *T. pallidum*-infected—was slightly superior, replication of *T. pallidum* occurred when other such as rat or hamster testis extract was substituted.

FIGURE LEGENDS

FIG. 1 Scanning electron micrographs of *T. pallidum*. (A) Sf1Ep cell with attached treponemes after 5 days' incubation. Bar=5 μm. (B) Same as in (A), showing large numbers of treponemes forming a microcolony (arrow in A). Bar=1 μm. (C) and (D) Colonies of *T. pallidum* after 7 days' incubation. Bar=1 μm.

FIG. 2 Scanning electron micrographs of *T. pallidum*. (A) Low-power view showing many colonies of *T. pallidum* after 9 days' incubation. Bar=20 μm. (B) High-power view of one colony (arrow) seen in (A). Bar=1 μm. (C) Low-power view after 12 days' incubation, showing one large colony (arrow), several smaller ones, and many individual treponemes. Bar=5 μm. Cell sheet is beginning to break up. (D) High-power view of large colony seen in (C), containing large numbers of treponemes. Bar32 1 μm.

DESCRIPTION OF THE PREFERRED EMBODIMENTS

Material and Methods

Figure 1:
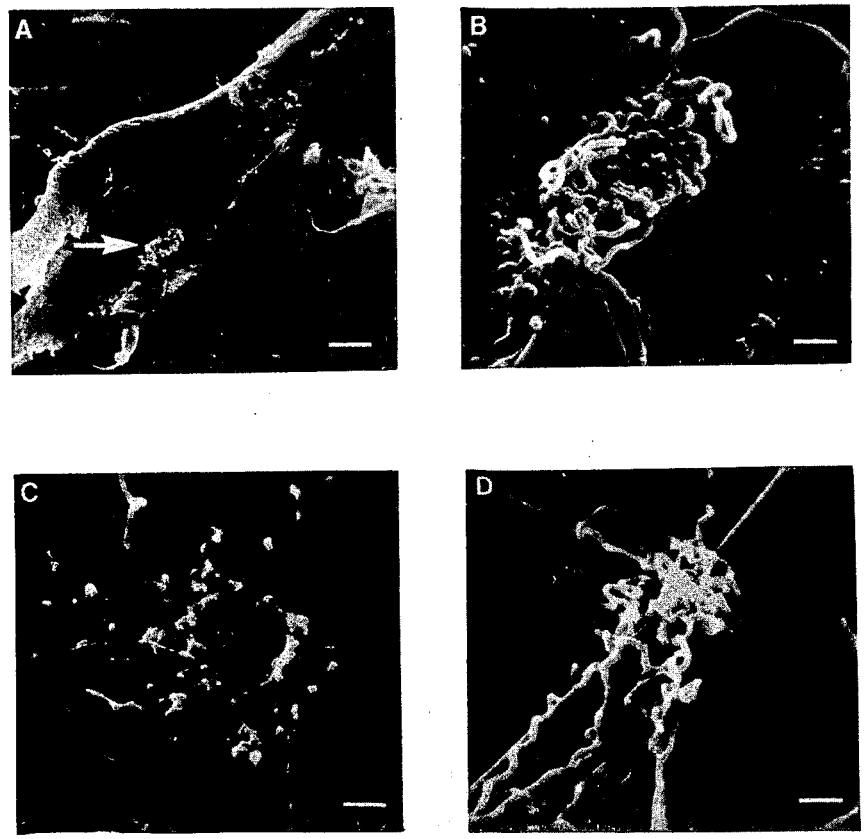
Figure 2:
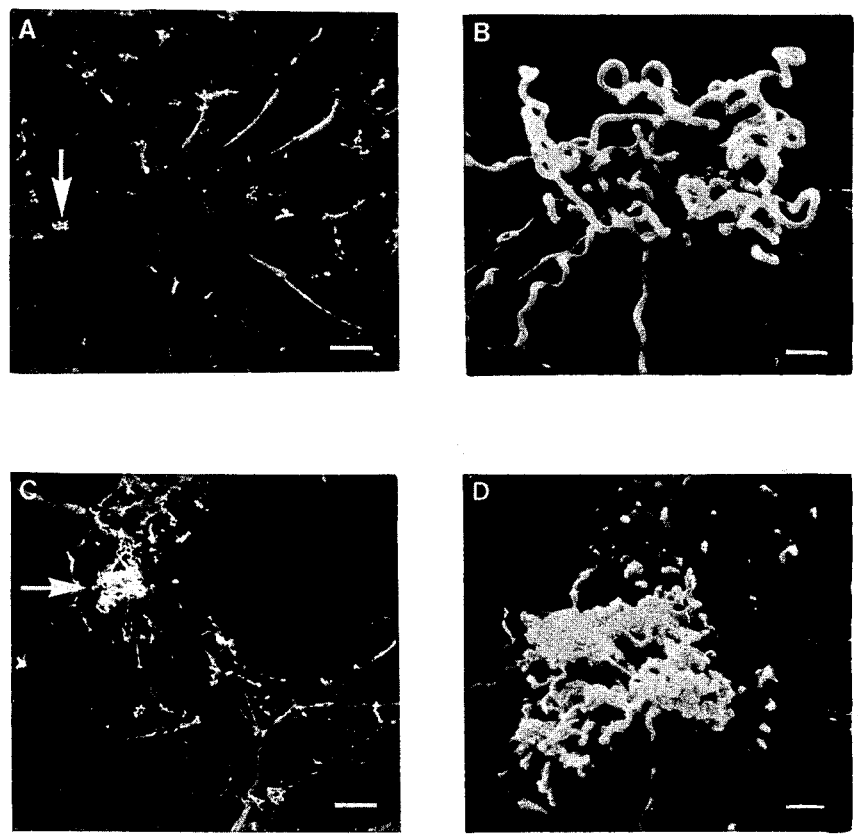

Rabbits. Six- to 8-month old New Zealand while males 3 to 4 kg and free of treponemal infection, as determined by nonreactivity to the VDRL test, were used for testicular passage and as a source of treponemes for inoculation into tissue culture.

Ten- to 12-week old females were used for determining virulence of *T. pallidum* after passage to tissue culture. The shaved backs of these animals were inoculated intracutaneously with 0.1 ml of various concentrations of *T. pallidum*.

All animals were housed individually at a temperature of 16 to 18 degrees C.

*T. pallidum.* The virulent Nichols strain was used throughout this work, and was maintained and passaged as described in Fieldsteel et al Infect. Immun. 18: 173–182 as cited above.

Fetal bovine serum (FBS). We have determined that commercial lots of FBS, although capable of supporting growth of mammalian cells, vary greatly in their ability to support survival of *T. pallidum.* Therefore all lots had to be compared with a lot known to support survival for at least two weeks. Acceptable lots were divided into aliquots sufficient for use in one experiment. The aliquots were then quick-frozen in a dry ice-alcohol bath and stored at $-20$ degrees C. until thawed at 37 degrees C. for use. While FBS is employed herein, calf serum is also effective.

Testis extract and tissue culture inocula. Rabbits were inoculated intratesticularly with $5\times10^7$ *T. pallidum.* On days 4 and 9 after inoculation, the rabbits were inoculated intramuscularly with 4 mg/kg of triamcinolone acetonide (Kenalog). The testes were removed aseptically 12 days (+1 day) postinfection at the time of peak orchitis. They were freed of extraneous tissue and minched finely with iris scissors. An individual testis was extracted with 5 ml of BRMM (Basal Reduced Medium, Modified; see below for preparation) in a 50-ml Fernbach flask. Air was displaced from the flask with 5% $CO_2$ in $N_2$. The flask was sealed with a silicone rubber stopper and placed in a shaking machine (118 oscillations/min) for 30 min at 33° C. The extract was then centrifuged at $500\times$ g for 5 min to remove gross particles, and the number of treponemes in the supernate was counted. This supernate was then diluted in fresh infected testis extract (ITE). The latter is the supernate of the infected extract centrifuged at $12,000\times$ g for 10 min. This treatment does not necessarily remove all of the treponemes in the supernate, but we have determined that the residue does not add significantly to the total number. Dilution with the ITE is such that 0.34 ml of the treponeme-containing extract contains the desired number of treponemes to be inoculated into each flask. Addition of this extract to 10 ml of BRMM, the amount used in tissue culture bottles, results in an ITE:BRMM ratio of 1:30, which was previously determined to be essential to the survival of *T. pallidum* in tissue culture as noted in Fieldsteel et al, supra.

Trypsin-Versene MEM (T-V MEM). This solution consists of $Ca^{++}$ and $Mg^{++}$-free minimum essential medium (MEM) containing 10 mg% of dithiothreitol (DTT), 20 mg% of crystalline trypsin, and 20 mg% of Versene (EDTA-ethylenediamine tetracetic acid, a chelating agent). With this solution it was possible not only to disrupt the cell monolayer, but also to separate the treponemes from the Sf1Ep cells. The latter were not removed from the suspension since they did not interfere with the counting of the treponemes.

Tissue culture procedures. Because of the many past failures to successfully cultivate *T. pallidum,* precise details of the method are presented. The tissue culture medium utilized for growing *T. pallidum* consisted of a modified Eagle's MEM plus FBS to a final concentration of 20%, and a 1:30 dilution of fresh ITE from rabbits.

The modified MEM is made by combining the following components in distilled water to a final volume of 100 ml: 10 ml of $10\times$ Earle's balanced salt solution without phenol red and $NaHCO_3$, 2 ml of $50\times$ MEM amino acids, 1 ml of $100\times$ MEM vitamins, 1 ml of 200 mM L-glutamine, 1 ml of $100\times$ MEM nonessential amino acids, and 1 ml of sodium heparin solution containing 100 U/ml. The solution is gassed briefly with $CO_2$; then 3.38 ml of $NaHCO_3$ (7.5%), 3.13 ml of 1M HEPES (organic buffer) 0.63 of resazurin (20 mg%), 10 mg of sodium pyruvate, 10 mg of DTT, and 150 mg of glucose are added. The solution is filter-sterilized, and 25 ml of heat-inactivated FBS is added. This culture medium, BRMM, was alluded to above. The flask of medium is then alternately evacuated and gassed with 5% $CO_2$/95% $N_2$ mixture 3 times and stored overnight before use.

Two days before infection with *T. pallidum,* 4-oz prescription bottles were seeded with $5\times10^5$ cells of Sf1Ep in MEM plus 10% FBS, and incubated at 33° C. The seed cultures of Sf1Ep were maintained as described in Fieldsteel et al, supra. Before inoculation of the treponemes, the growth medium was removed from the flasks and replaced with 10 ml of BRMM. The cultures were gassed with 5% $CO_2$/95%, $N_2$ for 1 minute at 3 liters/minute and allowed to equilibrate for 4 to 5 hours before inoculation. Each flask was then inoculated with 0.34 ml of testis extract containing the desired number of treponemes. The cultures were gassed for 1 minute with 1.5% $O_2$/5% $CO_2$/93.5% $N_2$ at 3 liters/minute. We had previously determined, in gradient cultures incubated under air, that the concentration of dissolved oxygen was approximately 1.5% in the area in the gradient that contained the greatest number and most active treponemes. Increasing the oxygen concentration to 3.5% resulted in both loss of viability and smaller increases in numbers of *T. pallidum.* Incubation was carried out at 33° C. Cultures were sacrificed at various intervals up to a maximum of 12 days, and treponemal counts made as follows: The medium was removed and saved. The monolayer was rinsed with 2 ml of T-V MEM, which was removed and combined with 1.25 ml of FBS. Additional T-V MEM (3 ml) was added to the flask, which was gassed with 5% $CO_2$/95% $N_2$ for 30 seconds, stoppered, and placed on a shaker for 20 minutes to remove the monolayer from the glass. The fluid containing suspended cells and treponemes was pipetted vigorously over the surface of the bottle to remove any adhering cells. This suspension was added to the previous rinse-serum mixture. The BRMM that had originally been removed from the monolayer was then added. Treponeme counts were made on triplicate samples from each flask as follows: A 10-$\mu$l aliquot was placed under a 22-$mm^2$ cover slip, and random fields were counted at a magnification of $\times800$ until at least 100 treponemes were counted or 50 fields were covered. The percentage of actively motile treponemes was calculated. Counts were made on two flasks per group on each day that counting was done.

Biochemical procedures. In each experiment, in order to substantiate observed increases in *T. pallidum*, assays were carried out to determine whether DNA also increased. The treponemal DNA was recovered using the following procedures. Duplicate cultures, both infected and uninfected, were harvested by the methods described above, and 1 ml was removed from the treponeme suspension for enumeration. The Sf1Ep cells were pelleted out of the remaining sample by centrifugation at 500× g for 15 minutes, and the top 13 ml of the samples were removed. Since 2.25 ml of the sample was left in the centrifuge tube, the Sf1Ep cell pellet remained undisturbed. Samples of supernatant were checked microscopically, and no Sf1Ep cells were detected. We found less than 5% difference between counts made initially and those made after removal of Sf1Ep cells. The treponemal fractions of duplicate bottles were pooled and centrifuged at 18,000× g for 20 minutes. The supernatant was removed and the treponeme pellet was fast-frozen immediately in a dry ice-alcohol bath and stored at −20° C. Uninfected cultures were treated in an identical fashion. DNA assays were performed simultaneously after all the samples in the same experiment had been collected.

The DNA from the thawed pellet was extracted by subjecting the treponemes to enzymatic digestion with lysozyme (0.5 mg/ml). They were then totally disrupted and homogenized by a brief sonic treatment at 4° C. The DNA was quantitated by the spectro-fluorometric technique of Labarca and Paigen. (Anal. Biochem. 102: 344–352, 1980). This method involves the reaction of DNA with the fluorescent dye bisbenzimide. The increase in fluorescence produced by an aliquot from the test samples was compared to that produced by a standard solution of DNA. The net treponemal DNA per flask was determined by subtracting the quantity of DNA in the control flasks from the quantity of DNA in the infected cultures. Since the pellet represented only 80% of the total number of treponemes obtained from the two bottles, the results were multiplied by 1.25 to determine the actual quantity of treponemal DNA present in the bottles.

Scanning electron microscopy (SEM). Sf1Ep cells were cultivated and inoculated with $1 \times 10^7$ *T. pallidum* as described above except that cover slips were placed in the culture vessels. Both infected and uninfected cover slips were removed after 5, 7, 9, and 12 days of incubation. They were fixed in 2% paraformaldehyde/2.5% glutaraldehyde in 0.1M phosphate buffer (pH 7.2) at 4 degrees C. for 45 minutes. They were then thoroughly washed with the phosphate buffer and dehydrated in a graded series of ethanol solutions (50%, 70%, 95%, 100%, 100%, 100%, 5 minutes each). The ethanol was replaced by the intermediate fluid, amyl acetate, through a graded series of ethanol/amyl acetate solutions (2:1, 1:1, 1:2, 100%, 100%, 100%, 100%, 5 minutes each). The amyl acetate was then replaced by the transition fluid, $CO_2$, in the bomb of a critical-point dryer (Technics). Following critical-point drying at 43 degrees C. and 1300 psi, the cover slips were mounted on aluminum microscope slides with conductive colloidal silver, and coated with a 200 Å layer of gold-palladium alloy (60:40 by weight) by triode sputtering (Polaron). Material thus prepared was examined in a Cambridge Mark IIa scanning electron microscope at an accelerating voltage of 10,000 eV, and a 30 degrees tilt. Micrographs were made with Polaroid Type 55 positive/negative black and white film.

In our own procedures in which gradient cultures of cottontail rabbit epithelium (Sf1Ep) were infected with *T. pallidum*, we were able to observe in all of the 25 experiments—apparent increased in numbers of attached treponemes. These increases ranged from 3- to 5-fold; however, since only about 5% of the inoculated treponemes attached to the cells, we did not observe an overall increase above that of the original inoculum. In contrast to the findings of others, we have never observed in vitro loss of virulence of *T. pallidum*. We now report unequivocal multiplication of virulent *T. pallidum* in the described tissue culture system, using Sf1Ep cells as substrate, under conditions of reduced oxygen tension (1.5%), the latter condition being extremely important and vital to the herein described invention.

RESULTS

Replication of virulent *T. palladium*. A series of seven experiments was carried out in an identical fashion according to the procedure outlined above. The results are summarized in Table 1. Significant increases in numbers occurred in every experiment when the inoculum was $1 \times 10^6$; these ranged up to a maximum of 100-fold, with an average increase of 49.3-fold after 9 days of incubation. With increasing inocula there was decreases in the fold increase until, with the $1 \times 10^8$ inoculum, little or no increase in the number of treponemes was observed. It is most striking that in all of the groups, irrespective of the inoculum, a ceiling of multiplication seemed to be imposed. Despite the 100-fold difference between the $1 \times 10^6$ and $1 \times 10^8$ inocula, the intergroup differences in the ceiling were remarkably small. The maximum ceiling was $1.0 \times 10^8$ for the $1 \times 10^6$ inoculum, $1.25 \times 10^8$ for the $2.5 \times 10^6$ inoculum, $1.35 \times 10^8$ for the $1 \times 10^7$ inoculum, and $2.37 \times 10^8$ for the $1 \times 10^8$ inoculum.

DNA assays on cultivated *T. pallidum*. The average quantities of treponemal DNA recovered from the cultures of the seven experiments are also presented in Table 1. In the first three experiments, the treponemal DNA content of cultures inoculated with 1.0 and $2.5 \times 10^6$ treponemes and incubated 1 day was slightly less than or equal to that of the negative controls. Because the treponemal DNA was insufficient to quantitate, these determinations were omitted from subsequent experiments. The net amount of DNA harvested from the infected cultures increased concurrently with the increase in numbers of treponemes in all inoculum groups. When the inoculum was $1 \times 10^6$, treponemal DNA increased from below the detectable limit of 0.05 μg per flask to 1.62 μg per flask on day 9, representing a minimum of a 33±10-fold increase.

The treponemes in the cultures inoculated with $10^6$ to $10^7$ organisms appeared to enter a logarithmic phase of growth after 1 to 2 days of incubation. The average DNA content of *T. pallidum* during that period was $3.14 \times 10^{-14}$ g per treponeme. The treponemes in cultures inoculated with $10^8$ organisms replicated very little, if at all, and the organisms appeared to be in a near stationary phase of growth. The average DNA content per treponeme was $1.88 \times 10^{-14}$ g, significantly lower than that found in the actively replicating treponemes.

Virulence of tissue culture-passaged *T. palladum*. In six of the seven experiments summarized in Table 1, treponemes harvested on the seventh day of incubation were inoculated intracutaneously into the shaved backs of rabbits, in serial 10-fold dilutions. This was done not only to confirm virulence, but also to determine the minimum number of tissue culture-grown *T. pallidum* required to produce typical treponeme-containing erythematous and indurated lesions. The results are shown in Table 2. In every instance the treponemes were virulent, with an average of 6.59 (range=1.52 to 18.5) organisms being required to produce a lesion.

SEM observation of *T. pallidum* in tissue culture. In an attempt to better understand attachment and replication of *T. pallidum* in cultures of Sf1Ep cells, we took a series of SEM photomicrographs at various times. FIGS. 1 and 2 are typical of what we observed during the course of incubation. Following attachment, colonies of treponemes apparently formed on the surface of the cells. Several of these colonies as well as individual treponemes, after 5 days of incubation, are seen under low magnification in FIG. 1A. FIG. 1B is a high-power view of one of the colonies seen in FIG. 1A. FIGS. 1C and 1D are high-power magnification of individual colonies, showing groups of intertwined treponemes after 7 days of incubation. The number of colonies increased with time of incubation; FIG. 2A (low magnification) shows many colonies after 9 days of incubation. One of them is seen under high magnification in FIG. 2B. These colonies as well as many individual treponemes that apparently washed off during the fixation procedure, were also observed under dark-field illumination.

At the twelfth day of incubation (FIG. 2C), the cell sheet started to deteriorate, the colonies apparently started to break up, and many more individual treponemes were seen. FIG. 2D is a high-power view of one of the large colonies seen in FIG. 2C.

Accordingly there is here a complete disclosure and evidence for what we blieve to be first successful in vitro cultivation of *T. pallidum*. It has thus been shown that under the conditions described herein, virulent *T. pallidum* attaches to and multiplies on the surface of Sf1Ep cells. In a series of seven experiments, it has been demonstrated that unequivocal replication occurred in each one. The extent of treponeme multiplication was dependent on that initial inoculum of *T. pallidum:* it was the greatest when that inoculum was $10^6$, and it was the least with an initial inoculum of $10^8$. Interestingly, the difference between these two inocula, 100-fold, was the maximum multiplication observed with the $10^6$ inoculum, although the average was 49-fold. With all of the inocula, the maximum ceiling of multiplication was approximately $1\text{–}2\times10^8$; therefore, the fold-increases of replication *T. pallidum* decreased with increasing inoculum size. Thus, when the initial inoculum was $2.5\times10^6$ *T. pallidum,* there was an average increase of 27.5-fold (range, 16- to 40-fold) by the ninth day after inoculation. When the inoculum was $1\times10^7$, the average increase was 11.8-fold (range, 7.8–15.3) on the ninth day after inoculation. With the $10^8$ inoculum, the greatest increase was 2.4-fold, indicating little or no replication.

It is important to know the reason for the apparent ceiling of multiplication, since it is relevant to further optimization of the culture system. It has been theorized that there are only limited sites of attachment on each cell, which would certainly limit replication. If this were true, we should have been able to increase the yield of treponemes by increasing the number of cells in the culture. However, when inoculated $2.5\times10^6$ treponemes into Sf1Ep cultures that were either 20 to 80% confluent the rates of growth were almost identical, and the maximum increased in *T. pallidum* were 24.0- and 20.2-fold, respectively, indicating that replication did not appear to be dependent on specific attachment sites on each cell. In fact, it appeared to be unrelated to cellular attachment per se.

The generation time of *T. pallidum* in rabbits has been postulated to be 30 to 33 hours. Hence, the theoretical maximum increase in *T. pallidum* during the period of observation in tissue culture would be about 100-fold in the cultures containing the $1\times10^6$ inoculum. This maximum was achieved in only one experiement, and although there was great variation in the maximum increases in *T. pallidum* from this inoculum, the average increase was approximately 49-fold. Therefore, increases from the $1\times10^6$ inoculum were not limited by attachment sites, but by the generation time. During the period in which *T. pallidum* is replicating, the Sf1Ep cell monolayer progresses from approximately 25% to 100% confluency; yet there was little difference in the number of attached organisms with an inoculum of $1\times10^8$. Five days after inoculation, the number of treponemes attached to the cells averaged $1.6\times10^8$. By the ninth day the number was almost identical, $1.7\times10^8$. On the twelfth day of incubation it had declined to $1.3\times10^8$. Perhaps of greatest significance is that in all of the inoculum groups, the viability of the treponemes had dropped off dramatically by the twelfth day of incubation. It seems likely that the ceiling of multiplication is due to a combination of factors, probably primarily to the exhaustion in the medium of some essential component(s) or the accumulation of toxic products. Since the Sf1Ep monolayer simultaneously deteriorated at the twelfth day of incubation, it was not possible to ascertain whether the treponemes, the cells, or both, were affected by these factors.

It seems likely that the testis extract is involved in the demise of treponemes, since this was one factor in the medium that could not be adequately controlled, varying from one experiment to another. We regard the testis extract as one of the three most important factors in the successful cultivation of *T. pallidum*. Additionally, we have determined that testis extract prepared from normal rabbits may be equally effective as that from infected rabbits.

A second, equally important factor in the cultivation of *T. pallidum* is careful selection of the fetal bovine serum used in both the extraction and cultivation media. Commercial lots of FBS vary greatly in their ability to support survival of *T. pallidum,* and may be so toxic as to kill off most of the treponemes after a few days in culture. The third important factor is the successful cultivation of *T. pallidum* is the amount of oxygen present in the system. We have determined, by actual measurement, that an atmosphere of 1.5% oxygen is optimal for replication of *T. pallidum*. In addition to, or in place of FBS, calf serum may be employed as well.

As further evidence that *T. pallidum* was replicating in the Sf1Ep cultures, we carried out concurrent DNA assays on the cultivated treponemes. We observed highly significant increases in treponemal DNA when the inocula ranged from $1\times10^6$ to $1\times10^7$, with the greatest increases, as might be expected, being in the former group. There was also excellent correlation in the amount of DNA per treponeme; the averages for the $1\times10^6$, $2.5\times10^6$, and $1\times10^7$ groups were $3.46\times10^{-14}$, $3.28\times10^{-14}$, and $2.79\times10^{-14}$ g per treponeme, respectively ($3.14\pm0.72\times10^{-14}$ g per treponeme). However, the average DNA per treponeme for the $1\times 10^8$ inoculum group ($1.88\pm 0.41\times 10^{-14}$ g) was considerably lower than that for the other grops. A phenomenon similar to to this has been observed in other bacteria. Gillies, N. E., and T. Alper, The Nucleic Acid Content of *Escherichia Coli* Strains B and B/R, Biochem, Biophys. Acta 43; 182-187, 1960 reported an increased DNA content per organism during logarithmic phase of growth for two strains of *E. coli*, which contained 1.4 to 1.8 times as much DNA per organisms during logarithmic phase of growth as during the stationary phase. It has also been reported that vegetative cells of *Bacillus megaterium* and B. cereus contained 2.3 and 3.3, respectively, times as much DNA as did their spores. In our experiments, the average DNA content per treponeme for the cultures inoculate with $10^6$ to $10^7$ organisms was 1.67 times that of treponemes from cultures inoculated with $10^8$ organisms. This difference is attributed to the different stages of growth the treponemes were in and falls within the range of increased DNA content reported for other bacteria in the logarithmic phase of growth.

In all of the experiments reported here involving single passage of *T. pallidum* in Sf1Ep cells, the organisms remained highly virulent for rabbits. The numbers required to produce treponeme-containing lesions were consistent with those reported for virulent *T. pallidum* passaged in vivo.

As demonstrated by scanning electron microscopy on *T. pallidum* during the course of replication in SfEp cells, microcolonies of treponemes are formed on the surface of the cells. These colonies, as well as many individual treponemes scattered across the cell surface, were also observed by dark-field illumination. Very few individual treponemes were seen by SEM before the twelfth day of incubation. This may have been due to their being washed off during the processing of the cover slips. However, on the twelfth day of incubation, many individual treponemes were seen in addition to the colonies. This also coincided with breaking up of the cell sheet and loss of viability of the treponemes.

Previous studies by others have been made of *T. pallidum* attachment to mammalian cells by SEM. Treponemes were observed only after a three-hour incubation period with cultured cells. Observations were also made up of 22 hours after coincubation of cells and treponemes. In both instances randomly attached treponemes were observed, but in no instance, was colony formation observed. It is assumed that the colonies probably form as the result of replication and therefore would not be observed under other conditions.

The extent of treponemal multiplication was evidently dependent on the initial inoculum of *T. pallidum;* it was greatest when that inoculum was $10^6$ and the least when the inoculum was $10^8$. However, with all of the inocula, the maximum ceiling of multiplication was $10^8$ to $2\times 10^8$. Thus, the fold increases of replicating *T. pallidum* decreased with increasing inoculum size. When the initial inoculum was $10^6$ *T. pallidum*, there was an average increase of 49-fold. When the inoculum was $10^7$, the average increase was 11.8-fold. With the $10^8$ inoculum the greatest increase was only 2.4-fold, indicating little or no replication. The ceiling of multiplication seemed likely due to a combination of factors, including exhaustion in the medium of some essential components, the accumulation of toxic products, or exhaustion of oxygen, which both cells and treponemes need for survival and replication.

Although replication was limited to some extent by the fact that the Sf1Ep cell sheet had started to deteriorate by the twelfth day of incubation, it seemed possible that by optimizing the culture conditions for both cells and treponemes, the treponemal yield could be increased. Toward that end we have now examined a number of parameters, including temperature, oxygen, serum, and rabbit testis extract requirements for the culture system.

In the optimization tests, the materials and methods employed were generally the same as described in detail above, except as noted hereinbelow.

Young male rabbits (6 weeks old), adult Lewis rats, and adult Golden Syrian hamsters were also used as a source of testis extract.

Tissue culture cells. An established cell line of cottontail rabbit epithelium (Sf1Ep) was used. It was received from Dr. W. A. Nelson-Rees, and was produced with support from the National Cancer Institute, Biological Carcinogenesis Branch, Division of Cancer Cause and Prevention, under the auspices of the Office of Naval Research and Regents of the University of California. Passage levels utilized in these experiments ranged between 73 and 85.

Serum. Fetal bovine serum (FBS) obtained from Flow Laboratories, Inc., Rockville, MD, was screened for suitability for use in tissue culture medium as described earlier. Calf serum obtained from Sterile Systems, Inc., Logan, Utah, was similarly tested for its suitability in this system and compared with a lot of FBS known to support replication of *T. pallidum*.

Testis extract and tissue culture inocula. The preparation of the testis extract has been described in great detail. Briefly, infected testes were minced finely, and each testis was extracted with 5 ml of the modified basal reduced medium (BRMM) for 30 minutes at 33° C., followed by centrifugation at $300\times g$ for 5 minutes to remove gross particles. The supernatant was then diluted to the approximate desired concentration using fresh infected testis extract, which was the supernatant of the infected extract centrifuged at $12,000\times g$ for 10 minutes (12K extract). An accurate final count was then made on this suspension since the 12K extract contains a small—but varying—number of treponemes. Dilution with the 12K extract was such that 0.34 ml contained the desired concentration of treponemes.

Addition of the 0.34 ml to 10 ml of BRNN, the amount used in tissue culture bottles, resulted in a testis extract:BRMM ratio of 1:30. Testis extract from *T. pallidum*-infected rabbits has been prepared on an empirical basis—one testis, irrespective of size, extracted in 5 ml of BRMM. This procedure remains unchanged. However, when comparing the suitability of uninfected rabbit testis, as well as testes preparations from rats and hamsters, as a substitute for the extract from infected rabbits, a weight/volume basis was established as follows. The total weight of both testes from a normal 6-month-old rabbit was 4.67 g. These testes were extracted in 10 ml of BRMM in the same manner as infected testes. On this basis, the weight/volume percent of the uninfected mature rabbit testis was 46.7g%. This, then, was the weight/volume percent basis for extracting testes from uninfected immature rabbits, mature rats, and mature hamsters. The 12K extracts, dilution of the inoculum, and inoculation of the bottles were the same as for infected 12K extract. These experiments were carried out at 33° C. under an atmosphere of 1.5% $O_2$.

The tissue culture procedures were the same as in the experiments and examples as described supra.

RESULTS

Effect of incubation temperature on replication of *T. pallidum*. We arbitrarily chose the temperature of 33° C. for all of our previous experiments because the optimum temperature for survival of *T. pallidum* was thought to be 35° C. or less. In attempts to experimentally determine the optimum temperature for replication of *T. pallidum*, we cultivated the organisms at temperatures ranging from 31° to 37° C., with the results shown in Table 3. Although minimal growth occurred at both extremes, it is apparent that the optimum temperature for replication ranged between 33° and 35° C.

Effect of atmospheric oxygen concentration on replication of *T. pallidum*. We previously had determined, in gradient cultures of Sf1Ep cells, that in the area in the gradient containing the greatest number of treponemes, the dissolved oxygen concentration was 1.5%. Therefore, we used that concentration throughout our studies without attempting to determine whether that concentration of oxygen was optimum in the present system in which *T. pallidum* was replicating. Experiments were carried out to determine the optimum concentration of oxygen for replication of *T. pallidum* was 33° C. Replication was examined in concentrations of oxygen ranging from <0.3% to 12.5% (Table 4). Some multiplication was observed in all concentrations except 12.5%. However, the concentrations of oxygen between 1.5 and 5% appeared to be within the optimum range for replication of *T. pallidum;* increases in numbers at those concentrations ranged from 22.4- to 27.7-fold.

Effect of temperature and oxygen variation on *T. pallidum* replication. The results of the previous experiments indicated that optimum growth of *T. pallidum* occurred at temperatures between 33° to 35° C. and at oxygen concentrations between 1.5 and 5%. We therefore carried out experiments at 33°, 34° and 35° C. utilizing oxygen concentration of 1.5, 3 and 5% with the results shown in Table 5. It is apparent that there was not much difference among the groups in replication of *T. pallidum*. The maximum fold-increases ranged from 18.9 in the 33° C. group incubated under 5% oxygen to 26.6 in the 34° C. group incubated under 3% oxygen. Variation in the oxygen concentration within each temperature group had little or no effect on replication. It did, however, affect motility, which invariably remained greater in the 5% oxygen concentration then in lower concentrations after 9 to 12 days of cultivation.

Effect of FBS concentration on *T. pallidum* replications. We had previously established in experiments carried out in gradient cultures that a 20% concentration of FBS in the BRMM was optimum for survival of *T. pallidum*. In the present system, where both tissue culture cells and treponemes were replicating and competing for this protein source, it was important to reinvestigate the requirements of the system for FBS. The results are shown in Table 6. Although replication of *T. pallidum* occurred in all concentrations of serum tested, the optimum concentration in this system was also 20%.

In addition to FBS we also investigated calf serum for its ability to support replication of *T. pallidum*. The results were not unlike those we obtained in earlier studies screening FBS for its ability to support survival of *T. pallidum*. We tested eight lots of calf serum, two of which did not support replication of *T. pallidum*. In three lots, increases ranged from 4.7- to 8-fold. In two other lots the increases were 9.1- and 9.8-fold. The eighth lot gave comparable results to the FBS control serum, with the average increase in treponemes being 13.7-fold in three experiments, compared to 16.5-fold in the FBS control.

Effect of various kinds of testis extract on replication of *T. pallidum*. Nelson had shown that extracts from rabbit testis—either normal of *T. pallidum*-infected rabbits—or from bull testes were an important factor for in vitro survival of *T. pallidum* in a cell-free system. We also found that infected rabbit testes extract was essential for prolonged survival of *T. pallidum* in gradient cultures of Sf1Ep cells. We therefore utilized it in the medium in our initial replication studies. However, we did not previously determine whether it was essential, or whether other extracts could be substituted. Table 7 summarizes the results of such recent experiments. It is clear that all of the testis extracts tested—*T. pallidum*-infected adult rabbit, normal adult rabbit, normal immature rabbit, adult rat, adult hamster—were capable of supporting replication of *T. pallidum*. When no extract was added, the number of treponemes increased by 10.7-fold, as compared to the 25.6-fold increase observed when extract from infected adult rabbit testis was added. This probably reflects the fact that because the inoculum is derived from rabbit testes, it cannot be eliminated entirely from the BRMM. In these experiments the final dilution of the extract in the "no extract" group was 1:537, compared to 1:30 for all the other groups.

Thus, it is now confirmed that *T. pallidum* replicates in cultures of Sf1Ep cells, and ranges of optimum conditions for in vitro replication of *T. pallidum* have been determined.

The optimum temperature for replication of *T. pallidum* has been the subject of numerous investigations. Turner and Hollander concluded that *T. pallidum* could multiply in vivo in the range of 30°–38° C., but that the optimum temperature level was probably 35°–38° C. For in vitro survival in cell-free cultures, the optimum temperature has been variously reported to be between 25° and 35° C.

In survival studies of *T. pallidum* in tissue culture, consideration had to be given to temperatures that would favor growth of the tissue cultures as well as the treponemes. In this regard, temperatures between 33° and 36° C. have been utilized. In the present investigation, the optimum temperature for replication of *T. pallidum* was found to be between 33° and 35° C. Although little or no multiplication occurred at 31° C., 58% of the treponemes survived at the twelfth day of incubation. At 37° C., the maximum increase occurred on the seventh day of incubation, but by the twelfth day none of the treponemes had survived.

Prior to 1974, *T. pallidum* was considered to be an anaerobic organism. Therefore, in most attempts to cultivate the organism, rigorous efforts were made to exclude oxygen because its presence was considered to be inimical to survival and growth. However, in 1974, Cox and Barber demonstrated that *T. pallidum* not only utilized molecular oxygen, but also contained an operating cytochrome oxidase system. Subsequently, varying concentrations of oxygen were included in tissue culture systems employed in attempts to cultivate or obtain prolonged survival of *T. pallidum*. We have now shown that *T. pallidum* is apparently a microaerophilic organism, replicating in atmospheres of oxygen ranging from <0.3% to 10%, but failing to survive in 12.5% oxygen.

The optimum oxygen concentration for replication at 33° C. ranged from 1.5 to 5%. However, in a series of experiments in which both temperature and oxygen concentrations were varied, it appeared that the optimal condition for replication of *T. pallidum* was incubation at 34° C. under an atmosphere containing between 3 and 5% oxygen.

In our earlier studies on survival of *T. pallidum* in gradient cultures of Sf1Ep cells, we established that 20% FBS was optimum for survival of the treponemes. In the current experiments, *T. pallidum* replicated in all concentrations of FBS from 5% to 30%, but we confirmed that the optimum concentration of multiplication was 20%. Because of the increasingly limited supplies of FBS, it was important to test other sources of serum. We found that when properly screened, calf serum was just as suitable as FBS for cultivation of *T. pallidum*.

One of the more important ingredients in the BRMM has been the rabbit testis extract. In all of our early experiments this was prepared from the infected testes used as the source of inoculum. The question then arose as to whether the extract had to be prepared from infected testis, adult testis, or indeed from rabbit testis at all. It was quite clear from the results of our current experiments that whatever was responsible for supporting replication was present in all rabbit, rat, and hamster testis preparations and was unrelated to either infection or species of animal utilized. The extract prepared from the infected-rabbit testis appeared to be slightly more effective than the other preparations. All of the extracts except that from infected testis were prepared on the same weight/volume basis, and therefore can be properly compared. The infected testes, irrespective of weight, were extracted in 5 ml of BRMM. Since these testes were at least twice as large as uninfected testes, the extract was generally more concentrated. Even in the absence of added testis extract we observed a 10.7-fold increase in treponemes, probably because the cultures contained extract present from the inoculum.

We have thus even further defined conditions for in vitro cultivation of *T. pallidum*. These results indicate that *T. palladium* is not as fastidious as formerly believed, since replication occurs under fairly wide ranges of temperature and oxygen concentrations.

This successful in vitro cultivation of *T. pallidum* now paves the way for biochemical, physiological and immunological studies on this organism, that were not possible previously.

TABLE 1

GROWTH OF T. PALLIDUM IN TISSUE CULTURES OF COTTONTAIL RABBIT EPITHELIUM (SflEp)[a]

| Inoculum | Day of Observation | Avg. No. of Treponemes/ Flask × $10^9$ (range) | Avg. Fold Increase (range) | % Motility (range) | μg DNA/Flask (Mean ± S.D.) | DNA/Treponeme × $10^{-14}$ g (Mean ± S.D.) |
|---|---|---|---|---|---|---|
| $1 \times 10^6$ | 5 | 1.59 (0.80–2.59) | 15.9 (8.0–25.9) | 90.5 (86.5–97.2) | 0.64 ± 0.25 | 3.76 ± 0.70 |
| | 7[b] | 3.27 (1.44–6.92) | 32.7 (14.4–69.2) | 87.8 (78.2–93.2) | 0.99 ± 0.38 | 3.25 ± 0.97 |
| | 9 | 4.93 (2.29–9.69) | 49.3 (22.9–96.9) | 72.2 (38.1–89.1) | 1.62 ± 0.54 | 3.43 ± 0.74 |
| | 12 | 4.91 (1.52–10.00) | 49.1 (15.2–100.0) | 30.6 (7.8–59.9) | N.D.[c] | N.D. |
| $2.5 \times 10^6$ | 5 | 2.57 (1.81–3.99) | 10.3 (7.2–16.0) | 90.5 (86.3–94.3) | 1.06 ± 0.31 | 3.91 ± 0.66 |
| | 7 | 4.97 (3.09–8.30) | 19.9 (12.4–33.2) | 80.2 (85.8–95.1) | 1.60 ± 0.33 | 3.31 ± 0.50 |
| | 9 | 6.88 (4.00–10.0) | 27.5 (16.0–40.0) | 73.7 (59.9–91.8) | 1.99 ± 0.53 | 2.96 ± 0.49 |
| | 12 | 6.06 (2.82–12.50) | 24.3 (11.3–50.0) | 28.4 (4.8–55.2) | N.D. | N.D. |
| $1 \times 10^7$ | 1 | 1.00 | — | N.D. | 0.33 ± 0.04 | 3.30 ± 0.34 |
| | 5 | 4.95 (3.87–6.00) | 5.0 (3.9–6.0) | 88.2 (90.1–86.3) | 1.51 ± 0.33 | 3.10 ± 0.80 |
| | 7 | 9.03 (8.10–11.30) | 9.0 (8.1–11.3) | 89.6 (85.1–93.8) | 2.16 ± 0.24 | 2.41 ± 0.32 |
| | 9 | 11.76 (7.75–15.30) | 11.8 (7.8–15.3) | 71.8 (54.2–90.8) | 2.56 ± 0.85 | 2.32 ± 0.18 |
| | 12 | 10.01 (6.57–13.50) | 10.0 (6.6–13.5) | 16.0 (5.3–35.6) | N.D. | N.D. |
| $1 \times 10^8$ | 1 | 10.0 | — | N.D. | 2.02 ± 0.23 | 2.02 ± 0.23 |
| | 5 | 16.01 (13.80–21.00) | 1.6 (1.4–2.1) | 82.4 (75.2–87.5) | 2.89 ± 0.75 | 1.66 ± 0.30 |
| | 7 | 17.48 (12.10–23.7) | 1.7 (1.2–2.4) | 76.6 (68.2–89.4) | 2.93 ± 0.26 | 1.76 ± 0.46 |
| | 9 | 16.80 (14.50–18.60) | 1.7 (1.5–1.9) | 66.9 (60.4–72.9) | 3.07 ± 0.55 | 1.83 ± 0.20 |
| | 12 | 13.41 (8.02–20.0) | 1.3 (.8–2.0) | 13.7 (2.6–36.2) | N.D. | N.D. |

[a]Combined data from seven separate experiments.
[b]In each experiment, organisms taken at this time produced treponeme-containing lesions in rabbits. It required an average of 6.59 treponemes (range = 1.52 to 18.5) to produce a lesion.
[c]Not done.

TABLE 2

Virulence of T. pallidum after one passage in SflEp cells[b]

| Exp. no. | Minimum no. of T. pallidum producing E.I.[b] | Day of lesion appearance |
|---|---|---|
| 1 | $1.85 \times 10^1$ | 26 |
| 2 | $3.02 \times 10^0$ | 30 |
| 3 | $1.52 \times 10^0$ | 22 |
| 4 | $6.69 \times 10^0$ | 15 |
| 5 | $1.75 \times 10^0$ | 35 |

TABLE 2-continued

Virulence of T. pallidum after one passage in SflEp cells[b]

| Exp. no. | Minimum no. of T. pallidum producing E.I.[b] | Day of lesion appearance |
|---|---|---|
| 6 | 8.06 × 10⁰ | 26 |

[a]Treponemes were harvested after seven days in culture, and serial 10-fold dilutions were inoculated intracutaneously into rabbits.
[b]Erythematous, indurated lesions containing T. pallidum.

TABLE 3

EFFECT OF TEMPERATURE OF INCUBATION ON REPLICATION OF T. PALLIDUM IN CULTURES OF SflEp CELLS

| Temperature (°C.) | Day of Observation | Avg. No. of Treponemes (× 10⁷) | Avg. % Motile | Avg. Fold-Increase |
|---|---|---|---|---|
| 31 | 5 | 0.65 | 60.2 | 1.3 |
|  | 7 | 0.78 | 68.1 | 1.6 |
|  | 9 | 0.95 | 69.5 | 1.9 |
|  | 12 | 0.69 | 58.1 | 1.5 |
| 32 | 5 | 1.54 | 80.4 | 3.1 |
|  | 7 | 2.75 | 87.6 | 5.6 |
|  | 9 | 4.35 | 84.3 | 8.8 |
|  | 12 | 4.74 | 71.3 | 9.7 |
| 33 | 5 | 2.23 | 89.1 | 4.5 |
|  | 7 | 4.61 | 91.5 | 9.4 |
|  | 9 | 7.89 | 90.2 | 16.1 |
|  | 12 | 7.08 | 45.4 | 14.5 |
| 34 | 5 | 3.89 | 92.5 | 7.9 |
|  | 7 | 6.43 | 87.9 | 13.1 |
|  | 9 | 9.51 | 72.8 | 19.3 |
|  | 12 | 5.54 | 22.6 | 11.3 |
| 35 | 5 | 4.80 | 93.7 | 9.8 |
|  | 7 | 8.46 | 86.2 | 17.2 |
|  | 9 | 9.47 | 59.4 | 19.3 |
|  | 12 | 5.82 | 8.8 | 11.9 |
| 36 | 5 | 4.03 | 92.3 | 8.2 |
|  | 7 | 6.33 | 77.4 | 12.8 |
|  | 9 | 5.44 | 32.6 | 11.0 |
|  | 12 | 2.98 | 0.6 | 6.1 |
| 37 | 5 | 2.16 | 75.4 | 4.3 |
|  | 7 | 2.77 | 35.9 | 5.5 |
|  | 9 | 1.45 | 3.6 | 2.9 |
|  | 12 | 0.89 | 0.0 | 1.8 |

[a]Combined data from three experiments. Inocula ranged from 4.78 × 10⁶ to 5.18 × 10⁶ (average = 4.92 × 10⁶) treponemes per bottle. Bottles contained an atmosphere of 1.5% $O_2$-5% $CO_2$-93.5% $N_2$.

TABLE 4

EFFECT OF ATMOSPHERIC OXYGEN CONCENTRATION ON REPLICATION OF T. PALLIDUM IN CULTURES OF SflEp CELLS[a]

| Atmospheric Oxygen Concentration[b] (%) | Day of Observation | Avg. No. of Treponemes (× 10⁷) | Avg. % Motile | Avg. Fold-Increase |
|---|---|---|---|---|
| <0.3 | 5 | 1.91 | 85.1 | 3.6 |
|  | 7 | 3.68 | 88.7 | 6.9 |
|  | 9 | 5.63 | 78.9 | 10.6 |
|  | 12 | 4.11 | 46.2 | 7.7 |
| 1.0 | 5 | 2.12 | 89.2 | 4.0 |
|  | 7 | 4.91 | 91.2 | 9.2 |
|  | 9 | 8.14 | 90.4 | 15.2 |
|  | 12 | 8.03 | 59.5 | 15.1 |
| 1.5 | 5 | 2.18 | 88.5 | 4.4 |
|  | 7 | 5.00 | 91.4 | 10.1 |
|  | 9 | 7.06 | 79.9 | 14.2 |
|  | 12 | 12.43 | 59.0 | 25.0 |
| 2.0 | 5 | 2.09 | 91.4 | 3.9 |
|  | 7 | 4.80 | 90.9 | 9.0 |
|  | 9 | 8.92 | 92.6 | 16.7 |
|  | 12 | 12.15 | 81.1 | 22.8 |
| 2.5 | 5 | 1.71 | 87.3 | 3.2 |
|  | 7 | 4.68 | 93.6 | 8.8 |
|  | 9 | 7.80 | 92.4 | 14.6 |
|  | 12 | 12.70 | 81.5 | 23.8 |
| 3.0 | 5 | 1.76 | 80.9 | 3.3 |
|  | 7 | 4.79 | 93.5 | 9.0 |
|  | 9 | 8.05 | 91.8 | 15.1 |
|  | 12 | 11.95 | 89.6 | 22.4 |
| 3.5 | 5 | 1.96 | 83.1 | 3.7 |
|  | 7 | 4.68 | 92.2 | 8.8 |
|  | 9 | 7.47 | 88.7 | 14.0 |
|  | 12 | 12.95 | 83.6 | 24.3 |
| 4.0 | 5 | 1.72 | 83.5 | 3.2 |
|  | 7 | 3.94 | 93.8 | 7.4 |
|  | 9 | 7.55 | 92.6 | 14.2 |
|  | 12 | 13.50 | 85.6 | 25.3 |
| 4.5 | 5 | 1.63 | 85.8 | 3.1 |
|  | 7 | 4.06 | 88.9 | 7.6 |
|  | 9 | 7.77 | 89.0 | 14.6 |
|  | 12 | 11.95 | 87.5 | 22.4 |
| 5.0 | 5 | 1.54 | 83.8 | 3.1 |
|  | 7 | 4.28 | 89.3 | 8.6 |
|  | 9 | 7.88 | 90.8 | 15.9 |
|  | 12 | 13.77 | 81.6 | 27.7 |
| 7.5 | 5 | 1.22 | 58.4 | 2.9 |
|  | 7 | 2.51 | 80.6 | 5.9 |
|  | 9 | 4.32 | 90.4 | 10.2 |
|  | 12 | 8.58 | 66.8 | 20.2 |
| 10.0 | 5 | 0.43 | 41.5 | 1.0 |
|  | 7 | 1.04 | 66.2 | 2.5 |
|  | 9 | 1.06 | 72.5 | 2.5 |
|  | 12 | 2.09 | 65.5 | 4.9 |
| 12.5 | 5 | 0.27 | 0 | — |
|  | 7 | 0.21 | 0 | — |

[a]Inocula ranged from 4.24 × 10⁶ to 5.48 × 10⁶ in three separate experiments. Temperature of incubation was 33° C.
[b]Gas mixture contained the indicated percent oxygen and 5% $CO_2$, with the remainder being $N_2$.

TABLE 5

EFFECT OF VARYING BOTH TEMPERATURE AND ATMOSPHERIC OXYGEN CONCENTRATION ON REPLICATION OF T. PALLIDUM IN CULTURES OF SflEp CELLS

| Incubation Temperature | Atmospheric Oxygen Concentration[a] (%) | Day of Observation | Avg. No. of Treponemes (× 10⁷)[b] | Avg. % Motile | Avg. Fold-Increase |
|---|---|---|---|---|---|
| 33° C. | 1.5 | 5 | 1.60 | 88.1 | 3.7 |
|  |  | 7 | 4.29 | 92.7 | 9.3 |
|  |  | 9 | 8.15 | 92.3 | 17.6 |
|  |  | 12 | 10.75 | 42.8 | 23.3 |
|  | 3.0 | 5 | 1.51 | 85.8 | 3.5 |
|  |  | 7 | 4.15 | 88.9 | 9.0 |
|  |  | 9 | 9.03 | 91.8 | 19.5 |
|  |  | 12 | 10.50 | 42.2 | 22.7 |
|  | 5.0 | 5 | 1.40 | 92.0 | 3.3 |
|  |  | 7 | 3.66 | 88.8 | 7.9 |

TABLE 5-continued
EFFECT OF VARYING BOTH TEMPERATURE AND ATMOSPHERIC OXYGEN CONCENTRATION ON REPLICATION OF T. PALLIDUM IN CULTURES OF SflEp CELLS

| Incubation Temperature | Atmospheric Oxygen Concentration[a] (%) | Day of Observation | Avg. No. of Treponemes ($\times 10^7$)[b] | Avg. % Motile | Avg. Fold-Increase |
|---|---|---|---|---|---|
| | | 9 | 8.74 | 91.1 | 18.9 |
| | | 12 | 8.68 | 66.0 | 18.8 |
| 34° C. | 1.5 | 5 | 3.35 | 88.2 | 7.3 |
| | | 7 | 6.85 | 88.0 | 14.8 |
| | | 9 | 10.45 | 39.8 | 22.6 |
| | | 12 | 7.95 | 4.4 | 17.2 |
| | 3.0 | 5 | 3.22 | 87.8 | 7.0 |
| | | 7 | 7.73 | 92.7 | 16.7 |
| | | 9 | 12.30 | 63.2 | 26.6 |
| | | 12 | 8.81 | 9.3 | 19.1 |
| | 5.0 | 5 | 2.98 | 87.3 | 6.5 |
| | | 7 | 7.93 | 92.1 | 17.2 |
| | | 9 | 12.20 | 83.0 | 26.4 |
| | | 12 | 10.72 | 35.6 | 23.2 |
| 35° C. | 1.5 | 5 | 3.69 | 89.7 | 8.0 |
| | | 7 | 10.89 | 89.1 | 23.6 |
| | | 9 | 11.10 | 57.2 | 24.0 |
| | | 12 | 6.92 | 5.3 | 15.0 |
| | 3.0 | 5 | 4.26 | 92.6 | 9.2 |
| | | 7 | 10.26 | 93.1 | 22.2 |
| | | 9 | 11.75 | 68.4 | 25.4 |
| | | 12 | 8.20 | 12.6 | 17.7 |
| | 5.0 | 5 | 3.18 | 93.7 | 6.9 |
| | | 7 | 8.17 | 93.3 | 17.7 |
| | | 9 | 11.02 | 81.5 | 23.9 |
| | | 12 | 9.94 | 30.8 | 21.5 |

[a]Culture flasks contained indicated concentration of oxygen and 5% $CO_2$, with the remainder being $N_2$.
[b]Average of two experiments. Inoculum was $4.62 \times 10^6$ T. pallidum per flask.

TABLE 6
EFFECT OF CONCENTRATION OF FETAL BOVINE SERUM (FBS) IN CULTURE MEDIUM ON REPLICATION OF T. PALLIDUM[a]

| Concentration of FBS (%) | Day of Observation | Avg. No. of Treponemes ($\times 10^7$) | Avg. % Motile | Avg. Fold-Increase |
|---|---|---|---|---|
| 5 | 5 | 1.23 | 71.0 | 2.6 |
| | 8 | 1.89 | 48.9 | 4.0 |
| | 12 | 4.29 | 68.4 | 9.1 |
| 10 | 5 | 1.14 | 78.5 | 2.4 |
| | 8 | 3.69 | 66.1 | 7.9 |
| | 12 | 4.80 | 69.6 | 10.2 |
| 15 | 5 | 1.74 | 89.4 | 3.7 |
| | 8 | 3.92 | 73.1 | 5.3 |
| | 12 | 7.51 | 69.6 | 16.0 |
| 20 | 5 | 1.89 | 88.5 | 4.0 |
| | 8 | 5.15 | 86.9 | 11.0 |
| | 12 | 9.65 | 53.3 | 20.5 |
| 25 | 5 | 1.93 | 85.3 | 4.1 |
| | 8 | 3.68 | 79.3 | 8.1 |
| | 12 | 6.44 | 55.4 | 13.7 |
| 30 | 5 | 1.58 | 90.0 | 3.4 |
| | 8 | 3.89 | 80.0 | 8.3 |
| | 12 | 6.36 | 55.1 | 13.5 |

[a]The culture medium was BRMM containing the indicated concentrations of FBS. Incubation was at 33° C. in an atmosphere of 1.5% $O_2$-5% $CO_2$-93.5% $N_2$. Inoculum was $4.70 \times 10^6$ T. pallidum.

TABLE 7
EFFECT OF VARIOUS KINDS OF TESTES EXTRACT ON REPLICATION OF T. PALLIDUM

| Animal from which Extract was Prepared[a] | Day of Observation | Avg. No. of Treponemes ($\times 10^7$) | Avg. % Motile | Avg. Fold-Increase |
|---|---|---|---|---|
| Adult rabbit, infected | 0 | 0.51 | — | — |
| | 5 | 2.51 | 88.5 | 4.9 |
| | 8 | 7.82 | 93.1 | 15.3 |
| | 12 | 13.05 | 71.4 | 25.6 |
| Adult rabbit, normal | 0 | 0.47 | — | — |
| | 5 | 2.07 | 90.6 | 4.4 |
| | 8 | 8.60 | 93.8 | 18.3 |
| | 12 | 10.85 | 65.2 | 23.1 |
| Immature rabbit, normal | 0 | 0.45 | — | — |
| | 5 | 1.82 | 85.4 | 4.0 |
| | 8 | 6.51 | 90.9 | 14.5 |
| | 12 | 9.22 | 67.5 | 20.5 |
| Adult rat | 0 | 0.48 | — | — |
| | 5 | 1.83 | 88.0 | 3.8 |
| | 8 | 6.12 | 92.7 | 12.8 |
| | 12 | 7.89 | 69.2 | 16.4 |
| Adult hamster | 0 | 0.46 | — | — |
| | 5 | 1.83 | 89.3 | 4.0 |
| | 8 | 4.40 | 90.2 | 9.6 |
| | 12 | 9.21 | 79.2 | 20.0 |
| No Added Extract[b] | 0 | 0.43 | — | — |
| | 5 | 0.94 | 83.1 | 2.2 |
| | 8 | 2.10 | 91.2 | 4.9 |
| | 12 | 4.48 | 67.7 | 10.7 |

[a]Each 12K extract was prepared from testis of indicated animal. Inoculum for each group was diluted from original infected-rabbit testis extract such that final concentration of each 12K extract in the culture medium was 1:30.
[b]Contained only extract that was present in inoculum. Dilution of the inoculum was in BRMM rather than testis extract. Final dilution of extract was 1:537 compared to 1:30 for other groups.

Although the invention has been described with respect to specific details of certain embodiments thereof, it is not intended that such details act as limitations upon the scope of the invention except insofar as set forth in the accompanying claims.

We claim:

1. A method for the cultivation and replication of virulent *Treponema pallidum* which comprises (a) inoculating a tissue culture comprising mammalian cells and medium wherein said medium comprises a modified Eagle's MEM plus screened fetal bovine ser to a final concentration of about 5% to about 30% and a dilution of about 1:30 of testis extract under a dissolved oxygen tension of about <0.3% to about 10% with a virulent strain of *Treponema pallidum,* and (b) culturing said inoculated medium for a time sufficient to allow replication.

2. The method of claim 1, in which the mammalian cells on which the *T. palladium* attach and replicate are of cottontail rabbit epithelium (Sf1Ep) growing in monolayer cultures.

3. The method of claim 1 in which the modified Eagle's MEM comprises the following components to a final volume of 100 ml: 10 ml of 10× Earle's balanced salt solution without phenol red and $NaHCO_3$, 2 ml of 50× MEM amino acids, 1 ml of 100× MEM vitamins, 1 ml of 200 mM L-glutamine, 1 ml of 100× MEM nonessential amino acids and 1 ml of sodium heparin containing 100 $\mu$/ml, which is then gassed with $CO_2$, following which are added 3.38 ml $NaHCO_3$ (7.5%), 3.13 ml of 1M HEPES (organic buffer), 0.63 ml of resazurin (20 mg%) 10 mg of sodium pyruvate, 10 mg of dithiothreitol, and 150 mg of glucose.

4. The method of claim 3 in which the obtained solution is filter-sterilized before the addition of 25 ml of heat-inactivated fetal bovine serum to form the culture medium BRMM (Basal Reduced Medium, Modified) which is alternately evacuated and gassed with 5% $CO_2$/95% $N_2$ mixture before use.

5. The method of claim 4 in which receptacles are seeded with $5 \times 10^5$ cells of the Sf1Ep in MEM plus 10% of the FBS as growth medium and incubated at 33 degrees C., after which the growth medium is removed and replaced with 10 ml of BRMM followed by gassing with 5% $CO_2$/95% $N_2$ for 1 minute at 3 liters/minute, equilibrated for 4 to 5 hours and inoculated with 0.32M1. testis extract and gassed for 1 minute with 1.5% $O_2$/5% $CO_2$/93.5% $N_2$ at 3 liters/minute and incubated at 33 degrees C.

6. The method of claim 5 in which the tissue culture inocula prepared by inoculating rabbits intratesticularly with $5 \times 10^7$ *T. pallidum,*—and on the 4th and 9th day thereafter, inoculated intramuscularly with 4 mg/kg of triamcinolone acetonide, the testes being removed asceptically at about the 12th day at the time of peak orchitis, said testes being minced finely, extracted with BRMM, air evacuated, oscillated, centrifuged, the supernatant thereof diluted in fresh ITE, the latter being the supernate of the infected extract centrifuged at $12,000 \times g$ for 10 minutes, wherein 0.34 ml of the treponeme-containing extract contains the desired number of treponemes to be introduced into each culture receptacle and wherein addition of said extract to 10 ml of BRMM gives the optimum ITE: BRMM ratio of 1:30 essential to the survival of *T. pallidum* in tissue culture.

7. The method of claim 6, wherein the initial inoculum of *T. pallidum* was of the order of $10^6$.

8. The method of claim 1 in which the strain is the virulent Nichols strain.

9. The method of claim 4 in which calf serum is employed in place of FBS.

10. The method of claim 6 in which testicular extract of normal rabbits is employed as a diluent in place of the ITE.

11. The method of claim 1 wherein testis extract is a member of a group including infected (ITE) or normal testis extract of adult rabbit, immature rabbit, adult rat and adult hamster.

12. The method of claim 1 in which the temperature range is from about 33° C. to about 35° C.

13. The method of claim 1 in which the concentration of FBS is about 20%.

14. The method of claim 1 in which the dissolved oxygen tension is from about 1.5% to about 5%.

15. The method of claim 1 wherein the incubation period is from about 9 days to about 12 days.

* * * * *